United States Patent
Ahn et al.

(10) Patent No.: US 8,628,493 B2
(45) Date of Patent: Jan. 14, 2014

(54) FLEXIBLE SPIRALLY-ROLLED POLYMER TUBE FOR MONITORING AND TREATMENT OF BRAIN INJURIES

(75) Inventors: Chong H. Ahn, Cincinnati, OH (US); Raj K. Narayan, Cincinnati, OH (US); Chunyan Li, Cincinnati, OH (US)

(73) Assignee: The Feinstein Institute for Medical Research, Manhasset, NY (US)

( * ) Notice: Subject to any disclaimer, the term of this patent is extended or adjusted under 35 U.S.C. 154(b) by 364 days.

(21) Appl. No.: 12/477,844

(22) Filed: Jun. 3, 2009

(65) Prior Publication Data

US 2009/0297574 A1 Dec. 3, 2009

Related U.S. Application Data

(60) Provisional application No. 61/058,241, filed on Jun. 3, 2008.

(51) Int. Cl.
*A61M 1/00* (2006.01)
*A61K 9/22* (2006.01)
*A61M 31/00* (2006.01)

(52) U.S. Cl.
USPC ............. 604/27; 604/890.1; 604/503; 604/65

(58) Field of Classification Search
None
See application file for complete search history.

(56) References Cited

U.S. PATENT DOCUMENTS

| | | | | |
|---|---|---|---|---|
| 4,706,671 A | * | 11/1987 | Weinrib | 606/159 |
| 4,950,232 A | * | 8/1990 | Ruzicka et al. | 604/43 |
| 5,201,901 A | * | 4/1993 | Harada et al. | 606/198 |
| 5,806,517 A | * | 9/1998 | Gerhardt et al. | 600/345 |
| 6,135,976 A | * | 10/2000 | Tachibana et al. | 604/21 |
| 6,458,231 B1 | * | 10/2002 | Wapner et al. | 156/173 |
| 7,476,326 B2 | | 1/2009 | Ahn et al. | |
| 7,524,464 B2 | | 4/2009 | Ahn et al. | |
| 2004/0172290 A1 | * | 9/2004 | Leven | 705/2 |
| 2007/0055271 A1 | * | 3/2007 | Schaller | 606/90 |

OTHER PUBLICATIONS

Li, C., Han, J. and C. Ahn. Flexible biosensors on spirally rolled micro tube for cardiovascular in vivo monitoring. Biosensors and Bioelectronics 22(2007): 1988-1993. Avaible online Oct. 18, 2006.*
Esashi, M. Microsensors and Microactuators for Biomedical Applications. May 8-14, 1994. Nanofabrications and Biosystems: Frontiers and Challenges Conference, Abstract, p. 38.*
Li, C. et al (2007). Flexible biosensors on spirally rolled micro tube for cardiovascular in vivo monitoring. Biosensors and Bioelectronics 22(2007): 1988-1993.*
Esashi, M. (1994) Microsensors and Microactuators for Biomedical Applications.*
C. Li, W. Jung, A. W. Browne, R. K. Narayan, C. H. Ahn, "A Smart Polymer Lab-on-a-Tube (LOT) with Spirally-Rolled Microchannels for In-Situ Brain Tumor Monitoring and Drug Delivery," 12th International Conference on Micro Total Analysis Systems (MicroTAS 2008), San Diego, CA, USA, Oct. 12-16, 2008.

(Continued)

*Primary Examiner* — Manuel Mendez
*Assistant Examiner* — Jenna Zhang
(74) *Attorney, Agent, or Firm* — Amster, Rothstein & Ebenstein LLP

(57) ABSTRACT

A flexible spirally-rolled polymer microtube for in vivo monitoring and treatment of brain injuries; the tube integrally comprising one or more microsensors and one or more microchannels, wherein the microsensors monitor one or more parameters and the microchannels are capable of delivering substances to the brain, removing substances from the brain, or both.

22 Claims, 5 Drawing Sheets

(56) References Cited

OTHER PUBLICATIONS

Chunyan Li, Jungyoup Han, Chong H. Ahn, "Flexible Biosensors on Spirally Rolled Micro Tube for Cardiovascular In Vivo Monitoring"; Microsystems and BioMEMS Laboratory, Department of Electrical & Computer Engineering & Computer Science, University of Cincinnati, Biosensors and Bioelectronics 22(2007), p. 1988-1993, Available online on Oct. 18, 2006.

M. M. Tisdall, M. Smith, "Multimodal Monitoring in Traumatic Brain Injury; Current Status and Future Directions"; British Journal of Anaesthesia 2007 99(1):61-67; Published Online Jun. 4, 2007.

Chunyan Li, Frank E Sauser, Richard G Azizkhan, Chong H Ahn, Ian Papautsky, "Polymer flip-chip bonding of pressure sensors on a flexible Kapton film for neonatal catheters"; Journal of Micromechanics & Microengineering, 2005; 15 1729-1735.

Chunyan Li, Pei-Ming Wu, Andrew Browne, Soohyun Lee, Chong H. Ahn, "Hot-Embossed Piezoelectric Polymer Micro-Diaphragm Arrays Integrated with Lab-on-a-Chip for Protein Analysis"; IEEE Sensors Conference, Atlanta, Georgia, USA, Oct. 28-31, 2007.

Chunyan Li, Chong H. Ahn, Lori A. Shutter, Raj K. Narayan, "Toward Real-Time Continuous Brain Glucose and Oxygen Monitoring with a Smart Catheter," Biosensors & bioelectronics 25(1):173-8, Sep. 15, 2009.

Chunyan Li, Pei-Ming Wu, Wooseok Jung, Chong H. Ahn, Lori A. Shutter, Raj K. Narayan, "A Novel Lab-on-a-Tube for Multmodality Neuromonitoring of Patients with Traumatic Brain Injury (TBI)," RSC Publishing, Lab on a Chip; vol. 9, No. 14, pp. 1973-2104; Jul. 21, 2009.

Chunyan Li, Pei-Ming Wu, Wooseok Jung, Chong H. Ahn, Lori A. Shutter, Raj K. Narayan, "A Novel Lab-on-a-Tube for Multimodal Monitoring of Patients with Traumatic Brain Injury," Transducers 2009, Denver, Colorado, Jun. 21-25, 2009.

Chunyan Li, Pei-Ming Wu, Soohyun Lee, Andrew Gorton, Mark J. Schulz, Chong H. Ahn, "Flexible Dome- and Bump-Shaped Piezoelectric Tactile Sensors Using PVDF-TrFE Copolymer," Journal of Microelectromechanical Systems, vol. 17, Issue 2, Apr. 2008, 20th IEEE International Conference on Microelectromechanical Systems (MEMS 2007), Kobe, Japan, Jan. 21-25, 2007.

Chunyan Li, Pei-Ming Wu, Jungyoup Han, Chong H. Ahn, "A Flexible Polymer Tube Lab-Chip Integrated with Microsensors for Smart Microcatheter," May 16, 2008; Biomed Microdevices (2008) 10:671-679.

* cited by examiner

FLEXIBLE SPIRALLY-ROLLED POLYMER TUBE FOR MONITORING AND TREATMENT OF BRAIN INJURIES

CROSS REFERENCE TO RELATED APPLICATIONS

This application claims priority to provisional patent application Ser. No. 61/058,241, filed Jun. 3, 2008.

TECHNICAL FIELD

The present invention relates generally to an apparatus for in vivo monitoring and treatment of brain injuries.

BACKGROUND OF THE INVENTION

The monitoring of intracranial pressure has been the standard of care in the management of traumatic brain injuries. However, elevated intracranial pressure is a rather late-stage indicator of a patient's status and probable outcome.

There is a need in the industry to both monitor a broader array of parameters of brain function and improve the ability to monitor such parameters in real time and in relation to one another. One such improvement is the spirally-rolled microtube of Li et al., "Flexible Microsensors on Spirally Rolled Micro Tube for Cardiovascular In Vivo Monitoring," *Biosensors and Bioelectronics* 22 (2007) 1988-1993.

There is also a need in the industry to more effectively deliver substances (e.g., drugs) to the brain to treat patients that have brain injuries, as well as a need to more effectively remove substances (e.g., cerebrospinal fluid) from the brain.

SUMMARY OF THE INVENTION

Accordingly, the present invention provides an apparatus for in vivo monitoring and treatment of brain injuries.

One embodiment of the invention provides a flexible spirally-rolled polymer microtube for in vivo monitoring and treatment of brain injuries, the tube integrally comprising one or more microsensors and one or more microchannels, wherein the microsensors monitor one or more parameters and the microchannels are capable of delivering substances to the brain, removing substances from the brain, or both.

DETAILED DESCRIPTION OF THE INVENTION

Definitions

Figure 1:
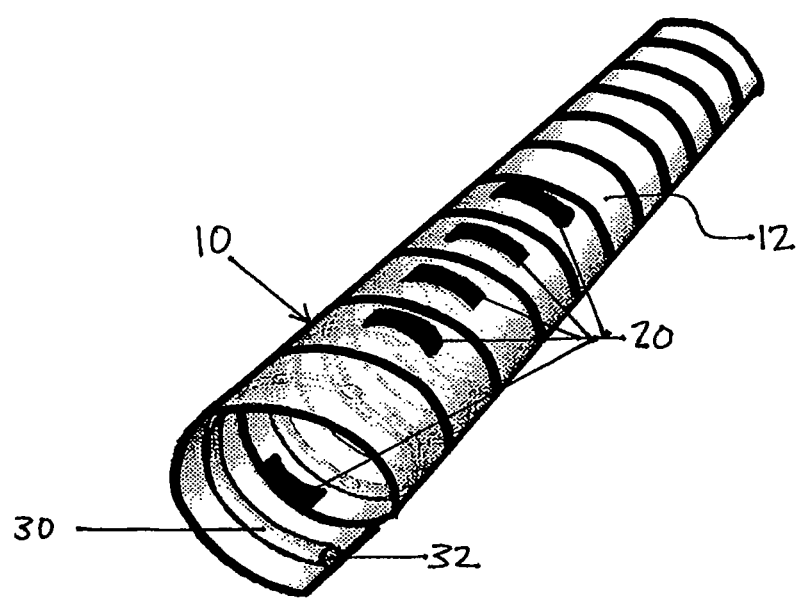
FIG. 1 is a schematic representation of an exemplary tube for in vivo monitoring and treatment of brain injuries according to an embodiment of the present invention.

The term "brain" as used herein refers to the brain or any portion of the brain, including, but not limited to, brain tissue, parenchyma, ventricles, intracranial spaces, intraventricular space, and intravascular space.

The term "brain injury" as used herein refers to any acute brain abnormality and includes, but is not limited to, traumatic brain injury, stroke, encephalitis, encephalopathy, hydrocephalus, anoxia, and poisoning.

The term "microsensor" as used herein refers to a micrometer or millimeter-sized device that performs one or more functions that include, but are no limited to, detecting, recording, measuring, or transmitting physical, biological, or chemical information or parameters via electrodes, membranes, and lead wires, each of which may or may not be integrated.

The process of "fabrication" as described herein relates to the process used for manufacture of micrometer and millimeter-sized features on a variety of substrates using standard fabrication techniques as understood widely by those skilled in the art. The process of fabrication typically involves a combination of processes such as thermoplastic fusion bonding, low temperature bonding using adhesives, and other processes commonly used for manufacture or microfabrication of MEMS (i.e., microelectromechanical systems) devices or electronic devices.

The term "microchannel" as used herein refers to a groove or plurality of grooves, or tunnels, created on a suitable substrate with at least one of the dimensions of the groove being in the micrometer or millimeter range. Microchannels may have widths, lengths, and/or depths ranging from 1 μm to 2000 μm. Microchannels can be used as stand-alone units or in conjunction with other microchannels to form a network of channels with a plurality of flow paths and intersections.

The term "bonding" as used herein refers to the process of joining at least two substrates, at least one of which has fabricated structures, e.g. a microchannel, on its surface to form a robust bond between the two substrates. A variety of techniques may be used to bond two substrates including thermoplastic fusion bonding, liquid adhesive assisted bonding, use of interfacial tape layers, etc.

The term "membrane" as used herein refers to components of the microsensors wherein a film of the materials is deposited on the substrate, more preferably on the electrodes of the microsensor, using a variety of techniques as well known in the art such as spin-coating, dip-coating, direct deposition, spray-coating, etc. Furthermore, the microsensor structure may be composed of multiple membranes.

The term "substance" as used herein refers to any substance that may conceivably be delivered to or removed from any portion of the brain, including, for example, brain tissue and intracranial space, or any portion of the microtube, including the microsensors. Examples of substances include, but are not limited to, drugs, chemicals, genes, cells, bodily fluids (including, e.g., cerebrospinal fluid), and calibration buffer solution (used to calibrate microsensors).

The intent of defining the terms stated above is to clarify their use in this description and does not explicitly or implicitly limit the scope of the claimed invention, which scope is defined solely by the claims.

An exemplary embodiment of an apparatus for in vivo monitoring and treatment of brain injuries is hereinafter described in detail in connection with the views and examples of FIGS. 1-5, wherein like numbers indicate the same or corresponding elements throughout the views.

One exemplary embodiment of a flexible spirally-rolled polymer microtube 10 for in vivo monitoring and treatment of brain injuries is illustrated in FIG. 1. Microtube 10 is constructed of one or more flexible polymer layers 12. Exemplary flexible polymers that are known to function effectively as layers upon which microsensors and microchannels can be fabricated prior to spiral-rolling such layers into a microtube 10 include, but are not limited to, polyimide, poly(p-xylene), and polyvinylidene fluoride trifluoroethylene (PDVF-TrFE). It is contemplated that other polymers may also function effectively, including, but not limited to, polylactic-co-glycolic acid (PLGA), polyethylene, polydimethylsiloxane (PDMS), and many electroactive polymers. It is further contemplated that additional polymers that will function effectively as a layers upon which microsensors and microchannels can be fabricated prior to spiral-rolling such polymer layers to form microtube 10 will be come available in the future.

If more than one polymer layer 12 is used to create microtube 10, multiple polymer layers may be fabricated to one another using techniques currently known to those skilled in the art, including, but not limited to, the techniques of polymer-to-polymer thermoplastic fusion bonding, solvent bonding, UV-adhesive assisted low temperature bonding, and adhesive bonding.

Thermoplastic fusion bonding involves heating two polymer layers to their glass transition temperature and then applying pressure to each polymer layer to force them into intimate contact, which causes bond formation. One example of adhesive bonding is stamp and stick bonding, wherein an adhesive is selectively applied, or "stamped," to one polymer layer and then a second polymer layer, which may be the same as the first polymer layer, is bonded, via "sticking," to the first polymer layer. Adhesives that are known to effectively bond polymer layers together include, but are not limited to, UV-adhesive, silicone, polyurethane, and epoxy. It is further contemplated that additional adhesives that effectively bond polymers will become available in the future.

In the present invention, individual microsensors 20 are fabricated on polymer layer 12 in plane, prior to spirally-rolling polymer layer 12. That is, microsensors 20 are fabricated upon polymer layer 12 while polymer layer 12 lies flat, using techniques that are well known to those skilled in the art.

Figure 2:
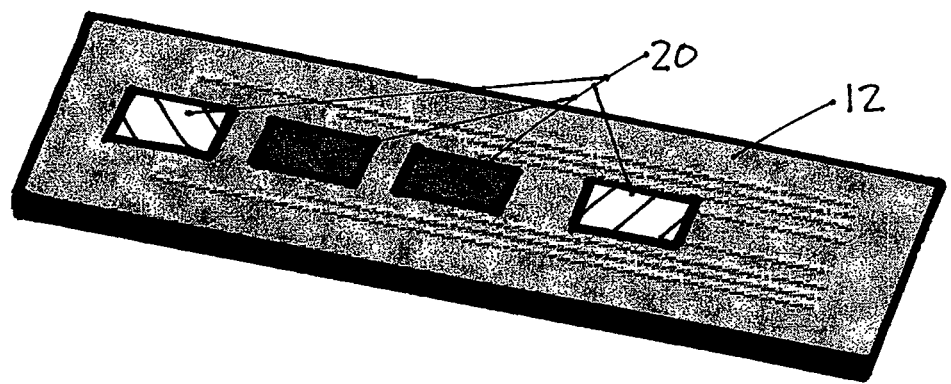
FIG. 2 is a schematic representation of an exemplary polymer substrate upon which microsensors have been fabricated prior to spirally-rolling such substrate into a tube for monitoring and treating brain injuries.

One or more microsensors 20 are fabricated upon polymer layers prior to spirally-rolling such layers to form microtube 10, as shown in FIG. 2. Microsensors 20 may be categorized by the parameter that they monitor or the mechanisms by which they operate to monitor such parameter. If categorized by the parameter they monitor, microsensors 20 that may be fabricated upon polymer layers prior to spirally rolling such layers to form microtube 10 include, but are not limited to, sensors that monitor any of the following: pressure, temperature, pH, glucose concentration, oxygen concentration, lactate concentration, pyruvate concentration, glutamate concentration, and carbon dioxide concentration. If categorized by the mechanism by which they operate, microsensors 20 that may be fabricated upon polymer layers prior to spirally-rolling such layers to form microtube 10 include, but are not limited to, amperometric, hot-wire anemometric, voltammetric, potentiometric, piezoelectric, piezoresistive, and capacitive sensors, resistance temperature detectors, and temperature sensitive resistors. Each of the above noted microsensors 20 is well known in the industry, as is the methodology that may be used to fabricate such microsensors upon a flexible polymer layer. It is contemplated that other microsensors 20 may also function effectively on microtube 10. It is further contemplated that additional microsensors 20 that may be fabricated upon microtube 10 will become available in the future.

Figure 3:
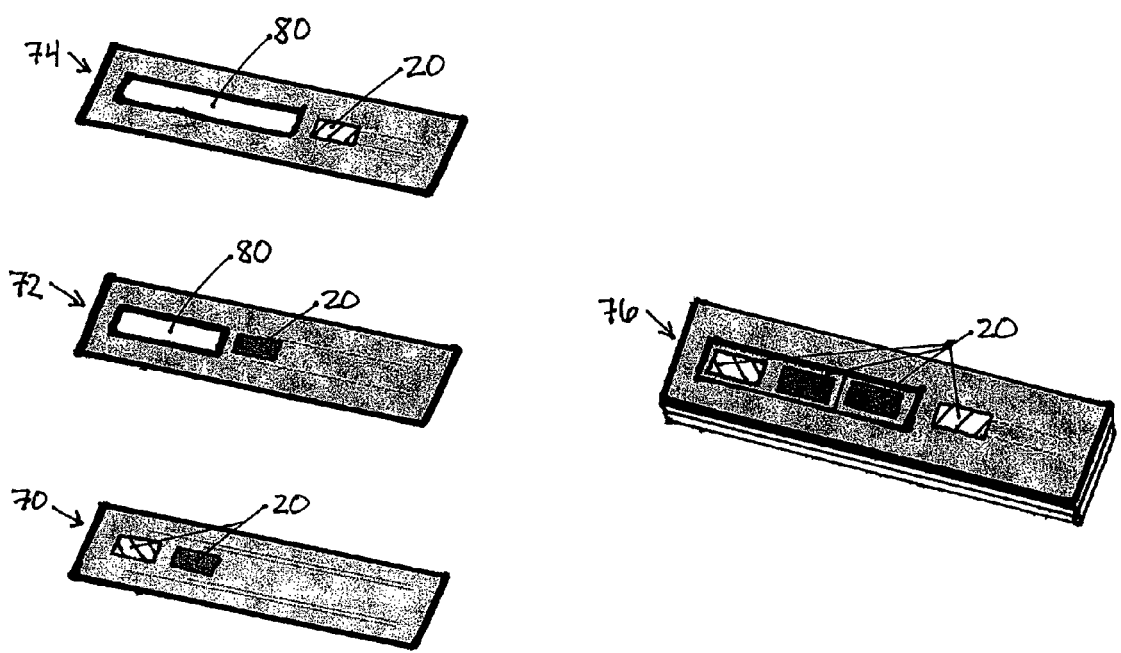
FIG. 3 is a schematic representation of the method of stamping and bonding.

Microsensors 20 for microtube 10 may all be fabricated upon a single polymer layer 12, as shown in FIG. 2. Alternatively, in a method called stacking and bonding, multiple layers of polymers, which may or may not be of the same polymer, may be used to create a multi-layer polymer substrate. FIG. 3 provides a schematic representation of this method. Microsensors 20 are fabricated upon the first, or base, polymer layer 70. Microsensors are also fabricated upon, in this example, a second polymer layer 72 and a third polymer layer 74, both of which have an open window 80 (i.e., a portion that has been removed from such polymer) so that microsensors 20 that are fabricated upon first polymer layer 70 will not be obstructed by second polymer layer 72 and microsensors 20 that are fabricated upon first polymer layer 70 and second polymer layer 72 will not be obstructed by third polymer 74 when the polymer layers are bonded to one another to form layered polymer substrate 76. Stacking and bonding multiple polymer layers allows for the inclusion of many more microsensors 20 than would be possible with only one polymer layer.

Polymer layers upon which microsensors 20 have been fabricated may be spirally-rolled in a manner that results in microsensors 20 on the exterior surface of the microtube 10, the interior surface of the microtube 10, or both.

Polymer layers may be spirally-rolled using any utensil that will allow the creation of a tube with an interior diameter. Examples of utensils that provide an adequate rolling surface are rods and needles. The interior diameter of the microtube need not be circular. It can also be rectangular, square, oval-shaped, etc.

Figure 4:
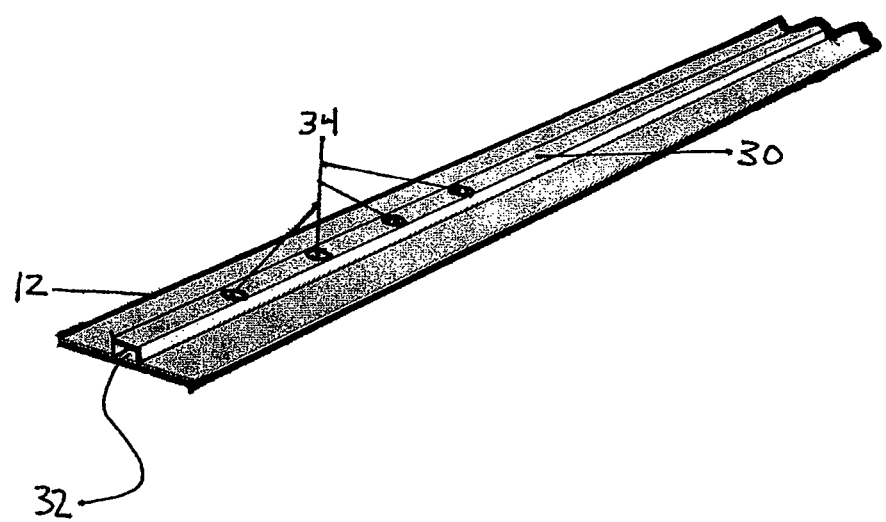
FIG. 4 is a schematic representation of an exemplary polymer substrate upon which microchannels have been fabricated prior to spirally-rolling such substrate into a tube for monitoring and treating brain injuries.

In the present invention, one or more microchannels 30 are fabricated upon one or more polymer layers 12 using known techniques prior to spirally-rolling such layers to form microtube 10, as shown in FIG. 4. The microchannel interiors 32 may be of any shape, including, for example, circular, square, or oval-shaped. Microchannel interiors 32 may also have varying sizes or shapes along their lengths.

Microchannels 30 are adapted and suitable for delivery or removal of minute volumes of substances and are typically designed to handle volumes ranging from the picoliter to the microliter range.

Microchannels 30 may each have one inlet or one outlet, or they may have a plurality of either or both. Microchannel openings 34 can serve as inlets at certain times and outlets at other times. For example, an opening at the distal end of microtube 10 may serve as an outlet if microchannel 30 delivers a substance (e.g., convection-enhanced delivery of a therapeutic agent) to the distal end of microtube 10, while that same opening may serve as an inlet if microchannel 30 removes a substance (e.g., drains cerebrospinal fluid) through that end of the microtube.

The inclusion of microchannels 30 in microtube 10 is a substantial improvement over the prior art.

First, microchannels allow in situ calibration of microsensors. In situ calibration is often required with sensors because of membrane biofouling and changes in the tissue surrounding the sensors that can result from the body's response to the insertion of a foreign body in the form of a microtube, catheter, scope, or similar device. Without calibration, sensors can experience large and unpredictable error and, as a result, provide inaccurate information. With traditional catheters, it is impossible to calibrate sensors once they are inserted. However, when microchannel outlets are fabricated at or near the microsensors on a spirally-rolled microtube, calibration buffer solution can be delivered to the site of the microsensors, which allows for in situ calibration of such microsensors, a significant and novel improvement.

Second, the inclusion of microchannels in the flexible spirally-rolled microtube also allows for organ or site-specific delivery and removal of substances such as drugs. With a traditional catheter, substances are delivered or removed through the lumen of the catheter, which, because of its size, results in significantly less precision than can be achieved with microchannels. The inclusion of microchannels in microtube allows precisely-controlled delivery of substances to very specific locations or precisely-controlled removal of substances from very specific locations. Microchannels also reduce the amount of dead volume. The inclusion of microchannels in the microtube of the present invention does not limit the functionality of the lumen of the microtube, which may also be used to deliver or remove substances to or from the brain.

Moreover, microchannels significantly reduce the amount of backflow, a problem that is commonly encountered with convection-enhanced delivery ("CED"). CED is a method of treating brain injuries by directly delivering substances to a site through the use of pressure gradients. CED leads to greater penetration of the substances into the targeted area and more uniform concentration profiles, but backflow can occur when tissue at the delivery site separates from the delivery device (e.g., catheter, needle), as a result of substance delivery that exceeds a certain rate. When backflow occurs, the substance flows preferentially back along the outside of the delivery device instead of infusing into the targeted area. Spirally-rolled microchannels are especially effective at CED, exhibiting less backflow than other delivery devices, including those with straight microchannels, with the same flow rate, pressure drop, or diameter, thereby representing a significant and novel improvement.

Spirally-rolled microchannels are superior to inline microchannels because each of the spirally-rolled microchannels may have multiple outlets that, when positioned properly, surround the targeted area. An inline microchannel can only target a single point, not an area. Therefore, treating an area may require several inline microchannels, but only one spirally-rolled microchannel.

The spirally-rolled microchannel's ability to precisely deliver substances to the microsensors also allows a clinician to deliver substances to the vicinity of the microsensors and monitor the brain's reaction to such substances via the microsensor response.

If two polymer layers 12 are used to construct microtube 10, one or both faces of one polymer layer will contain microchannel 30 and one face of the other polymer layer can be used to seal microchannel 30.

Polymer layers upon which microchannels 30 have been fabricated may be spirally-rolled in a manner that results in microchannels 30 on the exterior surface of the microtube 10, the interior surface of the microtube 10, or both.

Microchannels 30 may be attached to one or more drainage bags or other forms or reservoirs. Microchannels 30 may also be attached to dose control systems, which may enhance the CED capabilities of microchannels 30.

Figure 5:
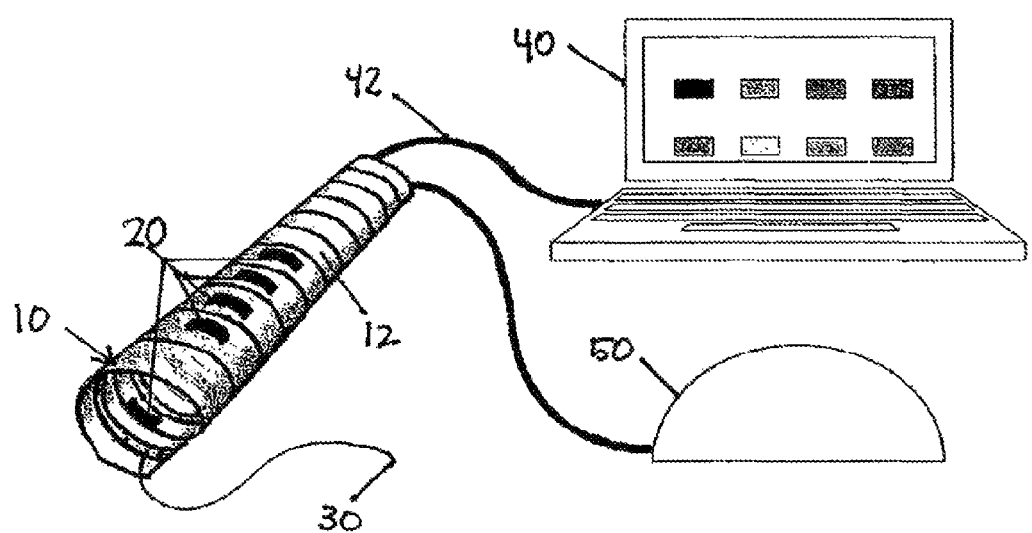
FIG. 5 is a schematic representation of an exemplary tube for monitoring and treating brain injuries, operatively coupled to a data acquisition device operating multimodality monitoring software and a dose control system.

FIG. 5 shows another exemplary embodiment of the present invention, in which microsensors 20 of microtube 10 are operatively connected to data acquisition device 40, which may operate multimodality monitoring software (e.g., NILabVIEW™, by National Intruments™). Data obtained by microsensors 20 is transmitted to data acquisition device 40 via signal conditioning device 42. Data acquisition device 40 may process the data it receives using multimodality monitoring software. The software allows users to monitor the data transmitted by the individual microsensors continuously in real time and allows users to monitor the data transmitted by the individual microsensors either in isolation or in relation to the data transmitted by other microsensors. For example, if the microtube of this invention contains temperature, pressure, and oxygen sensors, a clinician can monitor the temperature sensor or the pressure sensor or the oxygen sensor or, by using the software, the clinician monitor all three at once, including in relation to one another. The ability to continuously monitor multiple parameters in real time and in relation to one another allows clinicians to quickly assess brain injuries, develop treatment plans, and monitor the success of such treatment plans.

Also in FIG. 5, microchannels 30 of microtube 10 are in fluid communication with dose control system 50. Microchannels 30 may also be in fluid communication with reservoirs, drainage bags, or similar devices.

Microtube 10 can be used as the single parameter monitoring and substance delivery and removal system, or it can be used in combination with a stylet, catheter, endoscope, needle, or other similar device. Use of microtube 10 with such a device is facilitated by an adjustment of the diameter of microtube 10. A larger diameter allows microtube 10 to be slid over the end of such a device while a smaller diameter allows the microtube to be slid into the end of such a device. The device (e.g., catheter) may function as an additional substance delivery and removal system, an additional parameter monitoring system, a support for microtube 10, or any combination thereof.

The present invention is not limited to the monitoring and treatment of brain injuries. It may also be used to intravascularly monitor and treat conditions. Spirally-rolled microtubes with microsensors and microchannels may be provide excellent performance in intravascular use. The microtube of the present invention may be inserted into vessels including, but not limited to, arterial lines, jugular veins, and subclavian veins. It may be utilized to monitor and treat conditions that include, but are not limited to, general trauma, heart failure, and sepsis. It may also be used to monitor recovery following surgery. It is also contemplated that the microtube of the present invention may be utilized in research.

The following examples will serve to further typify the nature of this invention but should not be construed as a limitation of the scope thereof, which scope is defined solely by the claims.

EXAMPLE 1

Preparation of a Flexible Spirally-Rolled Polymer Microtube with Microchannels and Oxygen Sensors Poly(p-xylylene) microchannels are fabricated in plane upon a poly(p-xylylene) using polymer-to-polymer thermal bonding techniques. The microchannels were 5 cm long, 50 µm tall, and 100 µm to 400 µm wide. Oxygen sensors are fabricated in plane upon a 7.5 µm polyimide film according to known fabrication techniques. The poly(p-xylylene) film containing microchannels is bonded to the polyimide film containing microsensors with implantable grade silicone adhesive using known techniques. After bonding the polymer films to one another, the polymers are spirally-rolled over a 25 gauge needle. The needle is removed.

The flexible spirally-rolled microtube is sterilized in ethylene oxide gas at 50° C. for two hours and then inserted into agarose gel (0.6% w/v), which is prepared according to standard protocol and contained ultra-pure DNA-grade agarose powder and tris-borate-EDTA buffer solution. Flow in agarose gels mimics flow in living brain tissue. The temperature of the agarose gel is maintained at 37±1° C.

The response current of the oxygen sensors is measured three times per day. Response time averages 40 seconds and the sensors exhibit a sensitivity of 3.01±0.2 nA/mmHg.

Infusion of microchannel-delivered dye into the agarose gel via connection-enhanced delivery ("CED") is also measured. Infusion of dye at rates of 1.0, 2.0, 5.0, 7.5, 10, and 15 μl/minute for periods of up to 60 minutes results in spherically symmetric dye distributions around the microchannel outlet without evidence of backflow.

EXAMPLE 2

Preparation of a Flexible Spirally-Rolled Polymer Microtube with Temperature, Pressure, and Oxygen Microsensors In another exemplary embodiment, temperature, pressure, and oxygen microsensors are fabricated in plane onto PVDF-TrFE. The temperature sensor is a resistance temperature detector. The pressure sensor is piezoelectric and selectively DC-poled. The oxygen sensor is amperometric. After in plane fabrication of the microsensors upon the polymer, the polymer is spirally-rolled over a 25 gauge needle. The needle is removed and the microtube is connected to a data acquisition device that is operating multimodality monitoring software.

The microtube is immersed in artificial cerebrospinal fluid (147 mM NaCl, 3.5 mM KCl, 1.0 mM $CaCl_2$, 1.2 mM $MgCl_2$, 1.0 mM $NaH_2PO_4$, 2.5 mM $NaHCO_3$, with pH of 7.44), which is itself immersed in a water bath.

The temperature sensor is tested and quickly responds to initiated temperature changes of 25° C. to 45° C. in 5° C. increments.

Pressure of 5 mmHg is added periodically to the pressure sensor. The shift of resonant frequency of the pressure sensor is measured and exhibits a sensitivity of 0.38 MHz/mmHg.

The oxygen sensor is continuously monitored for a period of 20 hours a day for 5 days at −0.7 V. Output current reach 90% of the steady-state value in 18 seconds.

EXAMPLE 3

Preparation of a Flexible Spirally-Rolled Polymer Microtube with Glucose, Oxygen, Temperature, and Pressure Microsensors In another exemplary embodiment, a flexible spirally-rolled tube is fabricated with glucose, oxygen, temperature, and pressure sensors. The glucose and oxygen sensors are amperometric, the temperature sensor is a resistance temperature detector, and the pressure sensor is piezoelectric.

The glucose, oxygen, and temperature sensors are fabricated on 25 μm thick poly(p-xylylene) film. The pressure sensor is fabricated on 12 μm PVDF-TrFE film. The poly(p-xylylene) film and the PVDF-TrFE film are stacked upon one another and bonded with 35 μm thick silicone adhesive. The stacked, bonded films are spirally-rolled to form a microtube. The microtube is connected to a data acquisition device operating multimodality monitoring software.

The microtube is placed in a position such that the sensors nearest the distal end of the microtube were in a closed container filled with cerebrospinal fluid (discarded from patients with traumatic brain injuries) while the remaining sensors are positioned in 0.6% agarose gel.

The glucose sensors exhibit sensitivity of 79.9 nA/mM in the linear range of 0.1 mM to 10 mM.

The oxygen sensors exhibit similar responses in both CSF and agarose gel, exhibiting a sensitivity of 31.14 nA/mmHg. The sensors work at least five days with less than 9% sensitivity error.

Temperature sensors perform similarly in both CSF and agarose gel. They quickly respond to temperature changes with high linearity and sensitivity of 66.94 mV/° C. and are reliable from 30° C. to 42° C.

Static accuracy of the pressure sensors in both CSF and agarose gel is better than 0.5 mmHg in the range of 0 to 50 mmHg.

All documents cited in the application are, in relevant part, incorporated herein by reference; the citation of any document is not to be construed as an admission that it is prior art with respect to the present invention.

While the invention has been described with reference to certain embodiments, it is understood by those skilled in the art that various changes may be made and equivalents may be substituted without departing from the scope of the invention, as that scope is defined by the claims. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

We claim:

1. A flexible spirally-rolled polymer microtube for in vivo monitoring and treatment of brain injuries, the microtube integrally comprising one or more microsensors and one or more microchannels, wherein the microsensors monitor one or more parameters and the microchannels are capable of delivering substances to the brain and removing substances from the brain, and wherein the one or more microchannels is each from 1 μm to 2000 μm in length, width, and depth, and wherein each of the one or more microchannels has a microchannel interior, with each microchannel interior having at least two microchannel openings which are oriented perpendicular to a length along the longitudinal axis of the microchannel interior, wherein the microtube has an opening at each longitudinal end, and wherein the at least two microchannel openings extend inwardly toward a central axis of the longitudinal length of the microtube and away from a polymer layer of the microtube.

2. The microtube according to claim 1, wherein the microtube comprises one or more polymers selected from the group consisting of polyimide, poly(p-xylylene), and polyvinylidene fluoride trifluoroethylene (PDVF-TrFE).

3. The microtube according to claim 1, wherein the micro sensors comprise one or more pressure sensors, pH sensors, temperature sensors, glucose sensors, oxygen sensors, lactate sensors, pyruvate sensors, glutamate sensors, or carbon dioxide sensors.

4. The microtube according to claim 1, wherein one or more of the microsensors comprise amperometric, hot-wire anemometric, voltammetric, or potentiometric sensors.

5. The microtube according to claim 1, wherein one or more of the microsensors comprise pressure sensors selected from the group consisting of piezoelectric,
piezoresistive, and capacitive pressure sensors.

6. The microtube according to claim 1, wherein one or more of the microsensors comprise temperature sensors selected from the group consisting of resistance temperature detectors and temperature sensitive resistors.

7. The microtube according to claim 1, wherein one or more of the microsensors are fabricated on the exterior surface of the microtube.

8. The microtube according to claim 1, wherein one or more of the microsensors are fabricated on the interior surface of the microtube.

9. The microtube according to claim 1, wherein one or more of the microsensors are fabricated on the interior surface and one or more of the microsensors are fabricated on the exterior surface of the microtube.

10. The microtube according to claim 1, wherein one or more of the microsensors are operatively coupled to a signal conditioning device, a data acquisition device, or both.

11. The microtube according to claim 1, wherein one or more of the microsensors are operatively coupled to a data acquisition device operating multimodality monitoring software.

12. The microtube according to claim 1, wherein the data obtained by the microsensors is monitored in real time, continuously, or both.

13. The microtube according to claim 1, wherein one or more of the microchannels are fabricated on the exterior surface of the microtube.

14. The microtube according to claim 1, wherein the at least two microchannel openings are from two to four microchannel openings.

15. The microtube according to claim 1, wherein one or more of the microchannels are fabricated on the interior surface and one or more of the microchannels are fabricated on the exterior surface of the microtube.

16. The microtube according to claim 1, wherein one or more of the microchannels have a plurality of inlets, a plurality of outlets, or a plurality of both inlets and outlets.

17. The microtube according to claim 1, wherein one or more of the microchannels is capable of performing convection-enhanced delivery of substances to the brain.

18. The microtube according to claim 1, wherein one or more of the microchannels is in fluid communication with one or more dose control systems, drainage bags, or reservoirs.

19. The microtube according to claim 1, wherein the microtube is located or attached at or near the end of a stylet, needle, endoscope, or catheter.

20. The microtube according to claim 1, wherein the substances delivered to the brain and the substances removed from the brain are selected from the group consisting of drugs, chemicals, genes, cells, and calibrated buffer solution.

21. The microtube according to claim 20, wherein the substances delivered to the brain consists of the calibrated buffer solution for in situ calibration of the one or more microsensors.

22. A flexible spirally-rolled polymer microtube for in vivo monitoring and treatment of brain injuries, the microtube integrally comprising glucose, oxygen, temperature, and pressure microsensors and two or more microchannels, wherein the two or more microchannels are capable of delivering substances to the brain and removing substances from the brain, and wherein the two or more microchannels are each from 1 µm to 2000 µm in length, width, and depth and wherein each of the two or more microchannels has a rectangular microchannel interior having at least two microchannel openings, with each microchannel opening being oriented perpendicular to a length along the longitudinal axis of the microchannel interior, wherein the substances delivered to the brain and the substances removed from the brain are minute volumes of liquids or gases, wherein the microtube has an opening at each longitudinal end, and wherein the at least two microchannel openings extend inwardly toward a central axis of the longitudinal length of the microtube and away from a polymer layer of the microtube.

* * * * *